United States Patent [19]

Stout

[11] 4,235,789

[45] Nov. 25, 1980

[54] PROCESS FOR THE PREPARATION OF 1-AMINO-2-BROMO-4-HYDROXYAN-THRAQUINONE

[75] Inventor: James R. Stout, Hanahan, S.C.

[73] Assignee: Mobay Chemical Corporation, Pittsburgh, Pa.

[21] Appl. No.: 21,673

[22] Filed: Mar. 19, 1979

[51] Int. Cl.³ .............................................. C07C 97/25
[52] U.S. Cl. ..................................... 260/380; 260/381
[58] Field of Search ............................... 260/380, 381

[56] References Cited

U.S. PATENT DOCUMENTS

| | | | |
|---|---|---|---|
| 1,798,156 | 3/1931 | Gubelmann et al. | 260/380 |
| 2,134,654 | 10/1938 | Lulek | 260/381 |
| 2,604,480 | 7/1952 | Seymour et al. | 260/380 |
| 4,045,457 | 8/1977 | Gehrke et al. | 260/380 |

FOREIGN PATENT DOCUMENTS 2428337 12/1975 Fed. Rep. of Germany ........... 260/380

*Primary Examiner*—Winston A. Douglas
*Assistant Examiner*—Raymond K. Covington

[57] ABSTRACT

A process for preparing 1-amino-2-bromo-4-hydroxyanthraquinone by bromination of 1-aminoanthraquinone to 1-amino-2, 4-dibromoanthraquinone and subsequent hydroxylation (debromohydroxylation) of the resulting bromination product.

14 Claims, No Drawings

PROCESS FOR THE PREPARATION OF 1-AMINO-2-BROMO-4-HYDROXYANTHRAQUINONE

This invention relates to a one-pot-method for preparing 1-amino-2-bromo-4-hydroxyanthraquinone by bromination of 1-amino-anthraquinone to 1-amino-2,4-dibromoanthraquinone and subsequent hydroxylation (debromohydroxylation) of the resulting bromination product.

According to BIOS Final Report 1484, page 6, 1-amino-anthraquinone is brominated in 20% sulfuric acid at 70°–80° C. The resulting 1-amino-2,4-dibromoanthraquinone, after isolation and drying, is hydroxylated in concentrated sulfuric acid by exposure to sulfur trioxide in the presence of boric acid followed by dilution with water to yield the title compound (BIOS Final Report 1484, page 5).

This two step procedure is not advantageous because it requires isolation and drying of the inermediate 1-amino-2,4-dibromoanthraquinone.

It has now been found that 1-amino-2-bromo-4-hydroxy-anthraquinone can be obtained in good overall yield and purity by a process which comprises brominating 1-aminoanthraquinone in 70–95% sulfuric acid at elevated temperatures to obtain 1-amino-2,4-dibromoanthraquinone, which is then hydroxylated, without isolation, in the presence of sulfur trioxide and boric acid followed by adjusting the sulfuric acid content in the resulting mixture to 15–80% and isolating the precipitated 1-amino-2-bromo-4-hydroxyanthraquinone.

A preferred mode of the present invention is characterized by first reacting 1 part of 1-aminoanthraquinone with 1.8–3.0 moles of bromine per mole of 1-aminoanthraquinone in 4–8 parts of 70–95% sulfuric acid, preferably 85–93%, at temperatures between 60 and 140° C., preferably 80°–120° C., optionally in the presence of a halogenation catalyst, preferably iodine, over 4–18 hours, to yield 1-amino-2,4-dibromoanthraquinone in a reaction mixture whose sulfur trioxide concentration is then adjusted to 1–7%, preferably 2–5%, with sulfur trioxide or 20–65% oleum, followed by the addition of 1.2–3.5 moles, preferably 2.0–3.0 moles, of boric acid per mole of 1-amino-2,4-dibromoanthraquinone and heating at 100°–140° C., preferably 110°–130° C., over 8–18 hours followed by adjustment of the sulfuric acid concentration of the reaction mixture to 50–65% by the addition of water and/or dilute sulfuric acid or by drowning the reaction mixture into 50–65% sulfuric acid and subsequent or simultaneous adjustment to 50–65% sulfuric acid with water and/or dilute sulfuric acid.

Bromination may be accomplished by adding bromine and 1-aminoanthraquinone simultaneously at the beginning of the reaction or by successive addition of bromine over the course of the reaction. Normally bromine is added to the solution of 1-aminoanthraquinone in sulfuric acid.

In order to increase the bromine concentration of the reaction mixture, especially at elevated temperatures, the agitation of the reaction mixture can be advantageously carried out with a hollow stirring device having apertures in the shaft portion above the level of the liquid as well as in the blade below the liquid level. Bromine vapors are drawn through the upper apertures by the centrifugal action which results from the rotation of the blades and then exit into the reaction mixture via the apertures in the blades. Such a stirrer is known in Germany as "Begasungsruhrer".

The progress of the bromination may be followed by thin layer chromatography or high pressure liquid chromatography so as to insure that the byproducts, 1-amino-2-bromoanthraquinone and 1-amino-4-bromoanthraquinone, represent less than 1% of the product mixture. This is essential, since hydroxylation of these two products results in 1-amino-2-hydroxyanthraquinone and 1-amino-4-hydroxyanthraquinone respectively. Both products are isolated along with the desired 1-amino-2-bromo-4-hydroxyanthraquinone and therefore give rise to a product with unsatisfactory quality.

The hydroxylation of 1-amino-2,4-dibromoanthraquinone requires a certain concentration of sulfur trioxide as specified above. Due to the initially high concentration of sulfuric acid in the reaction mixture, the desired sulfur trioxide concentration can be achieved with relatively small quantities of commercially available oleum eg. 20–65% or sulfur trioxide. Again, thin layer chromatography and high pressure liquid chromatography are used to follow the progress of the reaction.

After completion of the reaction, the sulfuric acid concentration of the reaction mixture is adjusted to 15–80%, preferably 50–65%. The upper and lower limits of the sulfuric acid concentration determine the purity and yield of the precipitated 1-amino-2-bromo-4-hydroxyanthraquinone. Whereas certain applications require a highly pure 1-amino-2-bromo-4-hydroxyanthraquinone, other applications utilize material of a lower purity. The final sulfuric acid concentration is determined by the purity of the 1-amino-2-bromo-4-hydroxyanthraquinone required. Above 80% sulfuric acid, unacceptable losses of product occur, while below 50% sulfuric acid, byproducts, such as 1-amino-4-hydroxyanthraquinone, coprecipitate with the 1-amino-2-bromo-4-hydroxyanthraquinone. The latter condition yields a product whose quality is inadequate for certain applications. Concentrations of sulfuric acid in the range 50–65% yield a 1-amino-2-bromo-4-hydroxyanthraquinone which, after filtration, washing with water and drying at eg. 80° C. in vacuo, has a purity of up to 97%, as determined either by high pressure liquid chromatography or by thin layer chromatography and yields of 85–90% of theory. This 1-amino-2-bromo-4-hydroxyanthraquinone meets the requirements of most applications.

1-Amino-2-bromo-4-hydroxyanthraquinone is a well known starting material for preparing valuable dyestuffs especially disperse dyestuffs such as Disperse Red 60 and Disperse Red 159.

The following examples are given to further illustrate the invention.

EXAMPLE 1

100 g 1-aminoanthraquinone are charged to 600 g of 90% sulfuric acid at 30° C. 156 g bromine and 0.5 g iodine are added and the mixture is heated to 50° C. The reaction mixture is stirred at 50° C. for 4 hours and then heated to 80° C. After stirring for 2 hours at 80° C., the reaction mixture is cooled to 50° C. and an additional 30 g of bromine are added. After stirring for 2 hours at 50° C., the reaction mixture is heated to 80° C. and held, at this temperature, until a thin layer chromatogram indicates the absence of 1-aminoanthraquinone and monobrominated 1-aminoanthraquinone derivatives. 500 g of 65% oleum and 57 g of boric acid are then added and the reaction mixture is heated to 120° C. and held at this temperature for 6 hours. As heating progresses, bromine is condensed and collected. Approximately 80 g of bromine are recovered. The reaction mixture is then cooled to 70° C. and approximately 640 g of ice are added, over 2 hours, at 70° C. After stirring for 2 hours at 70° C., the reaction mixture is diluted with water until the filtrate of a filtered sample, has a specific gravity of 1.48–1.50 which is equivalent to approximately 57–59% sulfuric acid. The reaction mixture is filtered through a polypropylene or glass fiber filter at 70° C. and the resulting product is washed with water until the pH of the filtrate is 3–4 and thus essentially acid free. The 1-amino-2-bromo-4-hydroxyanthraquinone is dried at 80° C. in vacuo to yield 130 g of powder which has a purity of 95% and is equivalent to 87% of theoretical yield.

EXAMPLE 2

87 g (0.39 moles) 1-aminoanthraquinone are added to 306 g of 98% sulfuric acid at 30°–45° C. 140 g (0.88 moles) bromine are added and the reaction mixture is heated to 60° C. with stirring and held at 60° C. for 5 hours. The reaction mixture is then heated to 70°–75° C. and held at this temperature for 15 hours. The reaction mixture is cooled to 50° C., then 778 g of 24% oleum and 50 g (1.14 moles) boric acid are added while the temperature is kept between 30°–50° C. The reaction mixture is reheated to 115° C. and held at this temperature for 6 hours. The reaction mixture is then cooled to 30° C. and drowned into 400 g of 57% sulfuric acid. The sulfuric acid concentration is then adjusted to 57% by the addition of 904 g of water. The 1-amino-2-bromo-4-hydroxyanthraquinone is isolated by filtration through a glass fiber filter and the precipitate is washed with hot water until the pH of the filtrate is 3–4, which indicates that the precipitate is essentially free of sulfuric acid. After drying at 80° C., 118 g of product are obtained. This material has a purity of 95% and thus the yield is 86% of theory.

What we claim is:

1. Process for the preparation of 1-amino-2-bromo-4-hydroxyanthraquinone which comprises the steps of
   (a) brominating 1-aminoanthraquinone in 70–95% sulfuric acid at elevated temperatures to obtain 1-amino-2,4-dibromoanthraquinone;
   (b) without mixing the product of step (a) with sulfur trioxide and boric acid and hydroxylating;
   (c) adjusting the sulfuric acid content in the mixture obtained in step (b) to 50–80% and
   (d) isolating 1-amino-2-bromo-4-hydroxyanthraquinone.
2. Process according to claim 1 characterized in that bromination is carried out in 85–93% sulfuric acid.
3. Process according to claim 1 characterized in that bromination is performed at 60°–140° C.
4. Process according to claim 1 characterized in that bromination is performed at 80°–120° C.
5. Process according to claim 1 characterized in that the sulfur trioxide content in step (b) is adjusted to 1–7% (by weight) by the addition of oleum or sulfur trioxide.
6. Process according to claim 1 characterized in that the sulfur trioxide content in step (b) is adjusted to 2–5% (by weight) by the addition of oleum or sulfur trioxide.
7. Process according to claim 1 characterized in that hydroxylation with sulfur trioxide in the presence of boric acid is carried out at 110°–130° C.
8. Process according to claim 1 characterized in that the hydroxylation with sulfur trioxide is carried out in the presence of 1.2–3.5 moles boric acid per mole of 1-amino-2,4-dibromoanthraquinone.
9. Process according to claim 1 characterized in that the hydroxylation with sulfur trioxide is carried out in the presence of 2.0–3.0 moles boric acid per mole of 1-amino-2,4-dibromoanthraquinone.
10. Process according to claim 1 characterized in that, after reaction of the bromination product with sulfur trioxide in the presence of boric acid, the reaction mixture is drowned into 50–80% sulfuric acid followed by subsequent or simultaneous adjustment to 50–80% sulfuric acid with water or dilute sulfuric acid.
11. Process according to claim 1 characterized in that, after reaction of the bromination product with sulfur trioxide in the presence of boric acid, the reaction mixture is drowned into 50–65% sulfuric acid followed by subsequent or simultaneous adjustment to 50–65% sulfuric acid with water or dilute sulfuric acid.
12. The process according to claim 1 in which bromination is conducted with agitation in a hollow stirring device having apertures in the shaft portion above the liquid level as well as in the portion below the liquid level allowing bromine vapors to be drawn through the upper aperatures by centrifugal action of the lower portion and to exit into the reaction mixture through the apertures in the lower portion.
13. Process according to claim 1 characterized in that hydroxylation with sulfur trioxide in the presence of boric acid is carried out at 100°–140° C.
14. Process according to claim 1 characterized in that:
   bromination is carried out in 85–93% sulfuric acid at 80°–120° C. using 1.8–3 moles of bromine per mole of 1-aminoanthraquinone in 4–8 parts of sulfuric acid per part of 1-aminoanthraquinone; the sulfur trioxide content of the resulting reaction mixture is adjusted to 2–5%;
   hydroxylation is carried out at 110°–130° C. in the presence of 2.0–3.0 moles of boric acid per mole of 1-amino-2,4-dibromoanthraquinone;
   the resulting reaction mixture is drowned into 50–65% sulfuric acid and the sulfuric acid concentration is adjusted to 50–65% by the subsequent or simultaneous addition of water.

* * * * *